(12) United States Patent
Chen

(10) Patent No.: US 7,888,042 B2
(45) Date of Patent: Feb. 15, 2011

(54) METHODS FOR IDENTIFYING INSULIN MIMETICS

(75) Inventor: Xiaozhuo Chen, Athens, OH (US)

(73) Assignee: Ohio University, Athens, OH (US)

( * ) Notice: Subject to any disclaimer, the term of this patent is extended or adjusted under 35 U.S.C. 154(b) by 0 days.

(21) Appl. No.: 12/065,245

(22) PCT Filed: Aug. 31, 2006

(86) PCT No.: PCT/US2006/034423

§ 371 (c)(1),
(2), (4) Date: Sep. 2, 2008

(87) PCT Pub. No.: WO2007/028126

PCT Pub. Date: Mar. 8, 2007

(65) Prior Publication Data

US 2009/0203150 A1    Aug. 13, 2009

Related U.S. Application Data

(60) Provisional application No. 60/713,165, filed on Aug. 31, 2005.

(51) Int. Cl.
*G01N 33/53* (2006.01)
*G01N 33/556* (2006.01)
*G01N 33/566* (2006.01)
*C07K 14/62* (2006.01)
*C07K 14/705* (2006.01)

(52) U.S. Cl. .................... 435/7.1; 530/303; 530/350

(58) Field of Classification Search .............. None
See application file for complete search history.

(56) References Cited

PUBLICATIONS

Pillutla et al, 2002. Journal of Biological Chemistry. 277(25): 22590-22594.*
Li et al (2005. Biochemical and Biophysical Research Communications. 336: 430-437).*

\* cited by examiner

*Primary Examiner*—Bridget E Brunner
*Assistant Examiner*—Zachary C Howard
(74) *Attorney, Agent, or Firm*—Calfee, Halter & Griswold LLP

(57) ABSTRACT

Methods are provided for identifying and selecting candidate molecules that activate glucose transport through binding of the insulin receptor at a site other than the insulin binding site. The methods include analyzing the properties of one or more candidate molecules in terms of the ability to bind the insulin receptor and activate glucose transport. Optionally the methods include, competitive assays in the presence of the glucose receptor, a candidate molecule, and one or more of insulin, alpha PGG and beta PGG.

5 Claims, 8 Drawing Sheets

Amino acid sequence of insulin receptor: 1-27 signal peptide, 28-762 alpha subunit, 763-1382 beta subunit >gi|4557884|ref|NP_000199.1| insulin receptor [Homo sapiens]
MGTGGRRGAAAAPLLVAVAALLLGAAGHLYPGEVCPGMDIRNNLTRLHELENCSVIEGHLQILLMFKTRP
EDFRDLSFPKLIMITDYLLLFRVYGLESLKDLFPNLTVIRGSRLFFNYALVIFEMVHLKELGLYNLMNIT
RGSVRIEKNNELCYLATIDWSRILDSVEDNHIVLNKDDNEECGDICPGTAKGKTNCPATVINGQFVERCW
THSHCQKVCPTICKSHGCTAEGLCCHSECLGNCSQPDDPTKCVACRNFYLDGRCVETCPPPYYHFQDWRC
VNFSFCQDLHHKCKNSRRQGCHQYVIHNNKCIPECPSGYTMNSSNLLCTPCLGPCPKVCHLLEGEKTIDS
VTSAQELRGCTVINGSLIINIRGGNNLAAELEANLGLIEEISGYLKIRRSYALVSLSFFRKLRLIRGETL
EIGNYSFYALDNQNLRQLWDWSKHNLTTTQGKLFFHYNPKLCLSEIHKMEEVSGTKGRQERNDIALKTNG
DKASCENELLKFSYIRTSFDKILLRWEPYWPPDFRDLLGFMLFYKEAPYQNVTEFDGQDACGSNSWTVVD
IDPPLRSNDPKSQNHPGWLMRGLKPWTQYAIFVKTLVTFSDERRTYGAKSDIIYVQTDATNPSVPLDPIS
VSNSSSQIILKWKPPSDPNGNITHYLVFWERQAEDSELFELDYCLKGLKLPSRTWSPPFESEDSQKHNQS
EYEDSAGECCSCPKTDSQILKELEESSFRKTFEDYLHNVVFVPRKTSSGTGAEDPRPSRKRRSLGDVGNV
TVAVPTVAAFPNTSSTSVPTSPEEHRPFEKVVNKESLVISGLRHFTGYRIELQACNQDTPEERCSVAAYV
SARTMPEAKADDIVGPVTHEIFENNVVHLMWQEPKEPNGLIVLYEVSYRRYGDEELHLCVSRKHFALERG
CRLRGLSPGNYSVRIRATSLAGNGSWTEPTYFYVTDYLDVPSNIAKIIGPLIFVFLFSVVIGSIYLFLR
KRQPDGPLGPLYASSNPEYLSASDVFPCSVYVPDEWEVSREKITLLRELGQGSFGMVYEGNARDIIKGEA
ETRVAVKTVNESASLRERIEFLNEASVMKGFTCHHVVRLLGVVSKGQPTLVVMELMAHGDLKSYLRSLRP
EAENNPGRPPPTLQEMIQMAAEIADGMAYLNAKKFVHRDLAARNCMVAHDFTVKIGDFGMTRDIYETDYY
RKGGKGLLPVRWMAPESLKDGVFTTSSDMWSFGVVLWEITSLAEQPYQGLSNEQVLKFVMDGGYLDQPDN
CPERVTDLMRMCWQFNPKMRPTFLEIVNLLKDDLHPSFPEVSFFHSEENKAPESEELEMEFEDMENVPLD
RSSHCQREEAGGRDGGSSLGFKRSYEEHIPYTHMNGGKKNGRILTLPRSNPS

Fig. 5

Insulin receptor alpha subunit (Homo sapiens)
HLYPGEVCPGMDIRNNLTRLHELENCSVIEGHLQILLMFKTRPEDFRDLSFPKLIMITDYLL
LFRVYGLESLKDLFPNLTVIRGSRLFFNYALVIFEMVHLKELGLYNLMNITRGSVRIEKNNE
LCYLATIDWSRILDSVEDNHIVLNKDDNEECGDICPGTAKGKTNCPATVINGQFVERCWTHS
HCQKVCPTICKSHGCTAEGLCCHSECLGNCSQPDDPTKCVACRNFYLDGRCVETCPPPYYHF
QDWRCVNFSFCQDLHHKCKNSRRQGCHQYVIHNNKCIPECPSGYTMNSSNLLCTPCLGPCPK
VCHLLEGEKTIDSVTSAQELRGCTVINGSLIINIRGGNNLAAELEANLGLIEEISGYLKIRR
SYALVSLSFFRKLRLIRGETLEIGNYSFYALDNQNLRQLWDWSKHNLTTTQGKLFFHYNPKL
CLSEIHKMEEVSGTKGRQERNDIALKTNGDKASCENELLKFSYIRTSFDKILLRWEPYWPPD
FRDLLGFMLFYKEAPYQNVTEFDGQDACGSNSWTVVDIDPPLRSNDPKSQNHPGWLMRGLKP
WTQYAIFVKTLVTFSDERTYGAKSDIIYVQTDATNPSVPLDPISVSNSSSQIILKWKPPSDP
NGNITHYLVFWERQAEDSELFELDYCLKGLKLPSRTWSPPFESEDSQKHNQSEYEDSAGECC
SCPKTDSQILKELEESSFRKTFEDYLHNVVFVPRKTSSGTGAEDPRPSRKRR

Fig. 6

METHODS FOR IDENTIFYING INSULIN MIMETICS

PRIORITY

This application is the national stage of International Application No. PCT/US06/34423, filed Aug. 31, 2006, which claims the benefit of U.S. Provisional Application No. 60/713,165, filed on Aug. 31, 2005, the disclosure of which is incorporated by reference as if fully rewritten herein.

SEQUENCE LISTING

The instant application contains a Sequence Listing which has been submitted via EFS-Web and is hereby incorporated by reference in its entirety.

BACKGROUND

Diabetes mellitus, commonly called diabetes, refers to a disease process derived from multiple causative factors and characterized by elevated levels of plasma glucose, referred to as hyperglycemia. See, e.g., LeRoith, D. et al., (eds.), DIABETES MELLITUS (Lippincott-Raven Publishers, Philadelphia, Pa. U.S.A. 1996), and all references cited therein. According to the American Diabetes Association, diabetes mellitus is estimated to affect approximately 6% of the world population. Uncontrolled hyperglycemia is associated with increased and premature mortality due to an increased risk for microvascular and macrovascular diseases, including nephropathy, neuropathy, retinopathy, hypertension, cerebrovascular disease and coronary heart disease. Therefore, control of glucose homeostasis is an important approach for the treatment of diabetes.

There are two major forms of diabetes: Type 1 diabetes (formerly referred to as insulin-dependent diabetes or IDDM); and Type 2 diabetes (formerly referred to as noninsulin dependent diabetes or NIDDM). Type 1 diabetes is the result of an absolute deficiency of insulin, the hormone which regulates glucose utilization. This insulin deficiency is usually characterized by β-cell destruction within the Islets of Langerhans in the pancreas and absolute insulin deficiency. Type 2 diabetes is a disease characterized by insulin resistance accompanied by relative, rather than absolute, insulin deficiency. Type 2 diabetes can range from predominant insulin resistance with relative insulin deficiency to predominant insulin deficiency with some insulin resistance. Insulin resistance is the diminished ability of insulin to exert its biological action across a broad range of concentrations. In insulin resistant individuals the body secretes abnormally high amounts of insulin to compensate for this defect. When inadequate amounts of insulin are present to compensate for insulin resistance and adequately control glucose, a state of impaired glucose tolerance develops. In a significant number of individuals, insulin secretion declines further and the plasma glucose level rises, resulting in the clinical state of diabetes.

The majority of Type 2 diabetic patients are treated either with hypoglycemic agents which act by stimulating release of insulin from beta cells, or with agents that enhance the tissue sensitivity of the patients towards insulin, or with insulin. Sulfonylureas are examples of agents that stimulate release of insulin from beta cells. Among the agents applied to enhance tissue sensitivity towards insulin, metformin is a representative example. Even though sulfonylureas are widely used in the treatment of type II diabetes, this therapy is, in most instances, not satisfactory. In a large number of type II diabetic patients sulfonylureas do not suffice to normalize blood sugar levels and the patients are, therefore, at high risk for acquiring diabetic complications. Also, many patients gradually lose the ability to respond to treatment with sulfonylureas and are, thus, gradually forced into insulin treatment. This shift of patients from oral hypoglycemic agents to insulin therapy is usually ascribed to exhaustion of the pancreatic β cells in type II diabetic patients.

In addition to glucose transport, insulin is intimately involved in adipogenesis, a process which involves proliferation of preadipocytes (pre-fat cells) and differentiation of preadipocytes into adipocytes (fat cells) with accumulation of fat in adipocytes. As a result of its adipogenic effect, insulin has the undesirable effect of promoting obesity in patients with type 2 diabetes. (See, Moller, D. E. (2001) Nature 414: 821-827) Unfortunately, other anti-diabetic drugs which are currently being used to stimulate glucose transport in patients with type 2 diabetes also possess adipogenic activity.

The insulin receptor (IR) is a transmembrane receptor that is activated by insulin. It belongs to the large class of tyrosine kinase receptors. Two alpha subunits and two beta subunits make up the insulin receptor. The beta subunits pass through the cellular membrane and are linked by disulfide bonds. Tyrosine kinase receptors, including, the insulin receptor, mediate their activity by causing the addition of a phosphate groups to particular tyrosines on certain proteins within a cell. The "substrate" proteins which are phosphorylated by the Insulin Receptor include a protein called "IRS1" for "insulin receptor substrate 1". IRS1 binding and phosphorylation eventually leads to an increase in glucose transporter (GLUT4) molecules on the outer membrane of insulin-responsive tissues, including muscle cells, liver and adipose tissue, and therefore to an increase in the uptake of glucose from blood into these tissues. Briefly, the glucose transporter (GLUT4), is transported from cellular vesicles to the cell surface, where it then can mediate the transport of glucose into the cell.

Thus the main activity of activation of the insulin receptor is inducing glucose uptake. For this reason "insulin insensitivity", or a decrease in insulin receptor signaling, leads to Type II Diabetes—the cells are unable to take up glucose, and the result is hyperglycemia (an increase in circulating glucose), and all the sequelae which result from diabetes.

Accordingly, it is highly desirable to develop a new generation of anti-diabetic drugs that correct hyperglycemia that can activate the insulin receptor. Compounds that induce glucose uptake in a diabetic patient without causing hypoglycemia are particularly desirable.

SUMMARY OF THE INVENTION

Provided herein are methods for identifying and selecting candidate molecules that activate glucose transport through binding of the insulin receptor at a site other than the insulin binding site. The methods include analyzing the properties of one or more candidate molecules in terms of the ability to bind the insulin receptor and activate glucose transport. According to some embodiments, competitive assays that include the glucose receptor, a candidate molecule, and one or more of insulin, alpha PGG and beta PGG, are included in these methods.

BRIEF DESCRIPTION OF THE SEVERAL VIEWS OF THE DRAWINGS

The following detailed description of embodiments of the present invention can be best understood when read in conjunction with the following drawings, where like structure is indicated with like reference numerals and in which:

FIG. 5 shows the amino acid sequence (SEQ ID NO: 1) of insulin receptor: 1-27 signal peptide, 28-762 alpha subunit, 763-1382 beta subunit.

FIG. 6 shows the insulin receptor alpha subunit (SEQ ID NO: 2) (*Homo sapiens*).

DETAILED DESCRIPTION OF EMBODIMENTS

Figure 1A:
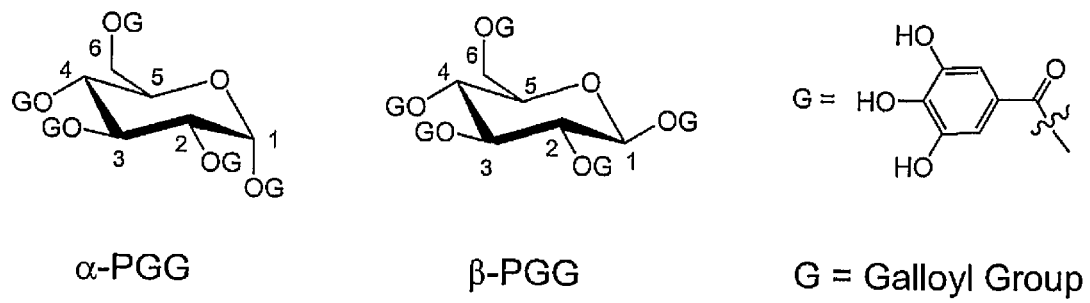
FIG. 1 shows α-PGG and β-PGG structures, and their ability to stimulate glucose transport (A) PGG consists of five gallic acid molecules esterified with glucose. Chemical synthesis yields both the α- and β-anomers of PGG. (B) Glucose transport stimulatory activity (13, 14) of PGG was assessed by incubating adipocytes in 6-well plates with insulin or PGG for 15 min followed by the addition of [$^3$H]-2-deoxy-D-glucose for 10 min before quantifying uptake (13, n=3, mean±SD, Two way-ANOVA, * P<0.05; ** P<0.01). α-PGG (●); β-PGG (□); insulin (○). (C) Glucose transport induced by insulin in the presence of α-PGG. One JAM of insulin was added to adipocytes in the presence of increasing amounts of α-PGG. After induction, radioactive glucose was added, and the glucose taken up by the cells was counted.

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are incorporated by reference in their entirety.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

The term "diabetes mellitus" or "diabetes" includes, but is not limited to, a disease or condition that is generally characterized by metabolic defects in production and utilization of glucose which result in the failure to maintain appropriate blood sugar levels in the body. The result of these defects is elevated blood glucose, referred to as "hyperglycemia." Two major forms of diabetes are Type 1 diabetes and Type 2 diabetes. As described above, Type 1 diabetes is generally the result of an absolute deficiency of insulin, the hormone which regulates glucose utilization. Type 2 diabetes often occurs in the face of normal, or even elevated levels of insulin and can result from the inability of tissues to respond appropriately to insulin. Most Type 2 diabetic patients are insulin resistant and have a relative deficiency of insulin, in that insulin secretion can not compensate for the resistance of peripheral tissues to respond to insulin. In addition, many Type 2 diabetics are obese. Other types of disorders of glucose homeostasis include impaired glucose tolerance, which is a metabolic stage intermediate between normal glucose homeostasis and diabetes, and gestational diabetes mellitus, which is glucose intolerance in pregnancy in women with no previous history of Type 1 or Type 2 diabetes.

The guidelines for diagnosis for Type 2 diabetes, impaired glucose tolerance, and gestational diabetes have been outlined by the American Diabetes Association (see, e.g., The Expert Committee on the Diagnosis and Classification of Diabetes Mellitus, Diabetes Care, (1999) Vol 2 (Suppl 1): S5-19).

The term "symptom" of diabetes, includes, but is not limited to, polyuria, polydipsia, and polyphagia, hyperinsulinemia, and hyperglycemia as used herein, incorporating their common usage. For example, "polyuria" means the passage of a large volume of urine during a given period; "polydipsia" means chronic, excessive thirst; "polyphagia" means excessive eating, and hyperinsulinemia means elevated blood levels of insulin. Other symptoms of diabetes include, for example, increased susceptibility to certain infections (especially fungal and staphylococcal infections), nausea, and ketoacidosis (enhanced production of ketone bodies in the blood).

The term "complication" of diabetes includes, but is not limited to, microvascular complications and macrovascular complications. Microvascular complications are those complications which generally result in small blood vessel damage. These complications include, e.g., retinopathy (the impairment or loss of vision due to blood vessel damage in the eyes); neuropathy (nerve damage and foot problems due to blood vessel damage to the nervous system); and nephropathy (kidney disease due to blood vessel damage in the kidneys). Macrovascular complications are those complications which generally result from large blood vessel damage. These complications include, e.g., cardiovascular disease and peripheral vascular disease. Cardiovascular disease refers to diseases of blood vessels of the heart. See. e.g., Kaplan, R. M., et al., "Cardiovascular diseases" in HEALTH AND HUMAN BEHAVIOR, pp. 206-242 (McGraw-Hill, New York 1993). Cardiovascular disease is generally one of several forms, including, e.g., hypertension (also referred to as high blood pressure), coronary heart disease, stroke, and rheumatic heart disease, Peripheral vascular disease refers to diseases of any of the blood vessels outside of the heart. It is often a narrowing of the blood vessels that carry blood to leg and arm muscles.

"Adipocytes" as used herein refers to fat cells. Morphologically, adipocytes are round-shaped, triglyceride (fat) vesicle-containing cells. Biochemically, adipocytes express high levels of insulin receptor on their cell surface and exhibit a highly active insulin-mediated glucose transport signaling pathway involving glucose transporter 4 (GLUT4). In vivo, adipocytes are involved in the synthesis and storage of fat (triglyceride) and glucose metabolism (uptake of glucose from blood and conversion of glucose into fat).

"Preadipocytes" as used herein refers to adipocyte precursor cells that, under the action of hormones such as insulin and glucocorticoid, divide and differentiate into adipocytes. Morphologically, preadipocytes are fibroblast-looking (thin, and spindle-shaped) and devoid of triglyceride (fat) vesicles in their cytoplasm. As compared to adipocytes, preadipocytes contain low levels of insulin receptor and relatively high levels of insulin-like growth factor 1 (IGF-1) receptors for receiving mitogenic and differentiating signals. Without induction or fall differentiation, preadipocytes do not express GLUT4 or other differentiation related genes such as PPAR-γ, C/EBP-α or C/EBP-γ. The intracellular glucose transport activity of preadipocytes is lower than that of adipocytes.

"Adipogenesis" as used herein refers to the process by which preadipocytes divide and differentiate into adipocytes.

"Lipogenesis" as used herein refers to the process by which fat is synthesized and accumulated in adipocytes.

The term "mammal" includes, without limitation, humans, domestic animals (e.g., dogs or cats), farm animals (cows, horses, or pigs), monkeys, rabbits, mice, and laboratory animals.

The present invention relates to methods and systems of identifying molecules that activate glucose transport in cells comprising an insulin receptor. Such molecules are expected to be useful for treating subjects with a hyperglycemic, hyperlipidemic and/or hyperinsulemic disorder.

In another aspect, the method comprises contacting a candidate molecule or a mixture of candidate molecules with an isolated polypeptide comprising the alpha 1,2,3,4,6-penta-O-galloyl-D-Glucopyranose (PGG) or beta PGG binding site of the insulin receptor and determining whether the candidate molecule or a plurality of the candidate molecules bind to one or both of the PGG binding sites. Binding of the candidate molecule to the alpha PGG or beta PGG or both binding sites indicates that the candidate molecule has the potential to activate glucose transport in a cell comprising the insulin receptor (IR). In certain embodiments, the method farther comprises comparing the binding of the candidate molecule and alpha PGG, beta PGG, or both, to the PGG binding site(s). In other embodiments, the method further comprises determining the biological effects of the candidate molecules and optionally comparing the biological effects of the candidate molecules to the biological effects of PGG.

The present invention is based, at least in part, on the inventors' discovery that alpha PGG and beta PGG bind to the extracellular alpha subunit of the insulin receptor and that the IR binding site for alpha PGG is not identical to the insulin binding site. The amino acid sequence of the insulin receptor, and more particularly the alpha subunit of the IR, are shown in FIG. 5 and FIG. 6. A discussion of the proposed binding insulin binding site on the IR is presented in Whittaker, J. and Whittaker, L., "Characterization of the Functional Insulin Binding Epitopes of the Full-length Insulin Receptor", (2005) J. Biol. Chem. Vol. 280, No. 22, pp. 20932-20936.

The present invention will now be described by reference to more detailed embodiments, with occasional reference to the accompanying drawings. This invention may, however, be embodied in different forms and should not be construed as limited to the embodiments set forth herein. Rather these embodiments are provided so that this disclosure will be thorough and complete, and will convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

All publications, patent applications, patents, and other references mentioned herein are incorporated by reference in their entirety.

EXAMPLES

Abbreviations: C/EBP-α, CCAAT/enhancer binding protein α; ddH$_2$O, double distilled water; HNMPA-(AM)$_3$, hydroxyl-2-naphthalenylmethylphosphonic acid triacetoxymethyl ester; HPLC, high performance liquid chromatography; ip, intraperitoneally; IR, insulin receptor; PGG, 1,2,3,4,6-penta-O-galloyl-D-glucose; PI 3-kinase, phosphatidylinositol 3-kinase; SPR, surface plasmon resonance; Sulfo-SANPAH, sulfosuccinimidyl-6-(4'-azido-2'-nitrophenylamino) hexanoate; TA, tannic acid; WGA, wheat germ agglutinin.

Cells. 3T3-L1 adipocytes, purchased from ATCC, were grown and maintained as fibroblasts in Dulbecco's modified Eagle's medium (DMEM) with high glucose in an incubator with 10% CO$_2$. Chinese hamster ovary cells that overexpress insulin receptor (CHO-IR) (23) were generously provided by Dr. Alan Saltiel's lab.

Reagents, compound synthesis, and glucose uptake assay. Bovine insulin was purchased from Sigma. PGG, in an approximate 1:1 mixture of α- and β-PGG, was synthesized from glucose in the non-radioactive form as described (22). The identity of the compounds was confirmed by MS and NMR. The compounds were dissolved in double distilled water (ddH$_2$O), filter sterilized, and stored as a 10 mM aqueous stock solution at −20° C. The stock solutions were diluted to final concentrations with sterile ddH$_2$O. Glucose uptake assays in 3T3-L1 adipocytes induced by PGG were performed as described (13).

Insulin signaling pathway study with inhibitors. To identify the signaling pathway and its potential protein target for PGG's glucose transport activity, three inhibitors to the insulin signaling pathway were selected. Hydroxyl-2-naphthalenylmethylphosphonic acid triacetoxymethyl ester (HNMPA-(AM)$_3$) (24), wortmannin (25), and cytochalasin B (26) inhibit the tyrosine kinase of the IR, phosphatidylinositol (PI) 3-kinase, and GLUT4, respectively. Inhibitors were individually added to the 3T3-L1 adipocytes along with either α-PGG or insulin at predetermined concentrations during glucose uptake assays, and the inhibition was measured by the glucose taken in by the cell samples treated with or without inhibitors.

Protein phosphorylation/activation and GLUT4 translocation. To investigate signal transduction induced by α-PGG, proteins from 3T3-L1 adipocytes or CHO-IR cells (23), which were treated with α-PGG or insulin for 15 min, were isolated, separated by PAGE, blotted on nylon membranes, and analyzed by Western blotting with antibodies against either IR or Akt. To measure PI-3 kinase activity, total proteins isolated from αPGG-treated adipocytes were assayed with $^{32}$P-γ-ATP as the phosphate donor and thin layer chromatography as the analysis method (27). For GLUT4 translocation studies, adipocytes, grown on 2-well Nunc chamber slides and incubated in the presence or absence of either insulin or α-PGG at 37° C. for 15 min, were immunostained after methanol and 4% paraformaldehyde fixation with a mouse monoclonal anti-GLUT4 antibody against a cytoplasmic epitope of rat/mouse GLUT4 (IF8, Biogenesis) followed by a treatment with secondary fluorescein (FITC)-conjugated affiniPure F(ad')$_2$ fragment donkey anti-mouse IgG (Jackson ImmunoResearch Laboratories). The stained cells were visualized and photographed with a laser scanning (confocal) microscope.

Insulin receptor binding studies. Surface plasmon resonance (SPR, 28) was used to detect the binding and binding affinity ($K_d$) between α-PGG and the pure recombinant glycosylated IR (R&D Systems, Inc.) using a BIAcore X (BIAcore, Inc.). The IR was bound to an NTA chip via IR's His tag. Increasing concentrations of α-PGG were injected into the system to allow interaction with the immobilized IR on the chip surface. After sensograms of α-PGG-IR binding at different concentrations were recorded, the binding affinity was analyzed using BIAevaluation software. Flowcells or channels without IR were used as negative control. To determine how α-PGG-binding affects insulin binding to the IR, total protein, with IR as a predominant receptor protein, was prepared from CHO-IR cells (23), and used to bind wheat germ agglutinin (WGA) wells of FlashPlates pre-coated with WGA (PerkinElmer Life Sciences, 29, 30) at 1 µg/well in 1× Binding Buffer (10×=100 mM Tris, 1.2 M NaCl, 50 mM KCl, 12 mM MgSO$_4$, 150 mM sodium acetate) at 4° C. for 6 h. After removal of unbound proteins and washes, either increasing (in saturation studies) or fixed amounts (in displacement studies) of insulin labeled with $^{125}$I (Amersham, 2000 Ci/mmol) was added to wells in the binding buffer with a final volume of 100 µL, with or without α-PGG. The plates were incubated at 4° C. overnight with gentle shaking. Following incubation and removal of unbound radioactive ligands, the wells were quickly washed with 3×200 µL of Wash Buffer (150 mM NaCl, 20 mM Hepes, pH 7.8, 0.025% Triton X-100). The bound ligand was detached (eluted) from the receptor with 2×200 µL 0.2M Glycine pH 2.8, and measured for its radioactivity using a Beckman Coulter LS 6400 Multi-Purpose Scintillation Counter. WGA wells coated with protein isolated from regular CHO cells served as controls for non-specific ligand binding. The receptor binding results were analyzed with the software GraphPad Prism.

For the cross-linking reaction, sulfosuccinimidyl-6-(4'-azido-2'-nitrophenylamino) hexanoate (Sulfo-SANPAH), a photoactive, non-cleavable cross-linker (31, 32) purchased from Pierce was used to cross link β-PGG to plasma membrane proteins that it interacts with. 3T3-L1 adipocytes were incubated with 200 µM α-PGG in pH 7.4 PBS for 2 h at room temperature with gentle shaking. Unbound α-PGG was removed by washing with ice-cold PBS, and the cells were treated in the dark with conjugation buffer containing 5 mM Sulfo-SANPAH. After 60 min of reaction, the cells were washed and irradiated with UV light (320-350 nm) for 15 min at 4° C. Cells were lysed and the total cell protein was isolated and separated on an 8% reducing SDS-PAGE, transferred to a nylon membrane, and analyzed with an anti-IR α-subunit antibody.

Animal studies. Genetically diabetic db/db mice or obese ob/ob mice were purchased from Jackson Lab. Male mice of 2-3 months of age were used. Unless otherwise stated, 10 mice (N=10) were used per group. α-PGG was either orally administered or intraperitoneally (ip) injected in the form of an aqueous solution at 20 mg/kg body weight with a 1-cc sterile plastic syringe. At different times after the α-PGG administration, blood or plasma was collected from the tail vein for measurement of glucose and insulin concentrations using commercial kits. Vehicle (aqueous solution) treated mice were used as controls and were statistically compared with the α-PGG treated mice. All animal studies were conducted in accord with the Ohio University guidelines for the use and care of laboratory animals.

Statistics analysis. All relevant assays and animal study data were analyzed with 1-way or 2-way ANOVA. In all figures, values are means±standard deviations of samples. Samples were replicated either in duplicate or triplicate in each experiment which was repeated at least 3 times. $P \leq 0.05$ was set as the level of significant difference.

The following examples show various combinations of the insulin receptor and one or more of alpha or beta PGG and insulin combined under conditions suitable for permitting specific intermolecular interaction. Generally, assay conditions involving these and potential candidate molecules are well known in the art. The below described examples provide guidance regarding the conditions under which intermolecular interactions may be assessed, of course there are other methods and conditions for assessing intermolecular interactions (including assessment of binding kinetics and competitive binding) that are well known in the art, though not described herein.

Example 1

α- and β-PGG Stimulate Glucose Transport in 3T3-L1 Adipocytes

Figure 1B:
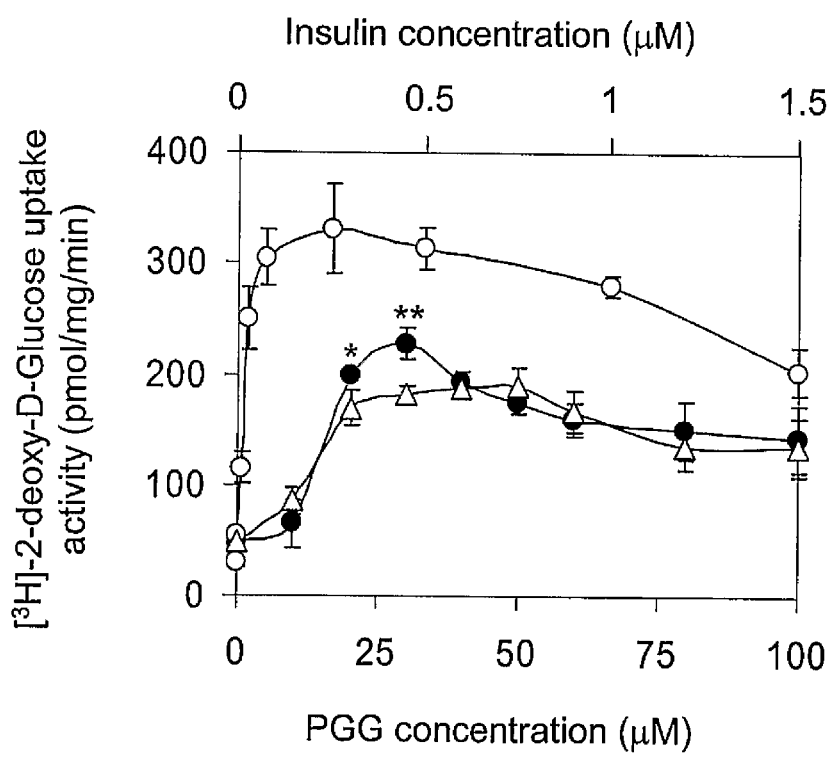
Figure 1C:
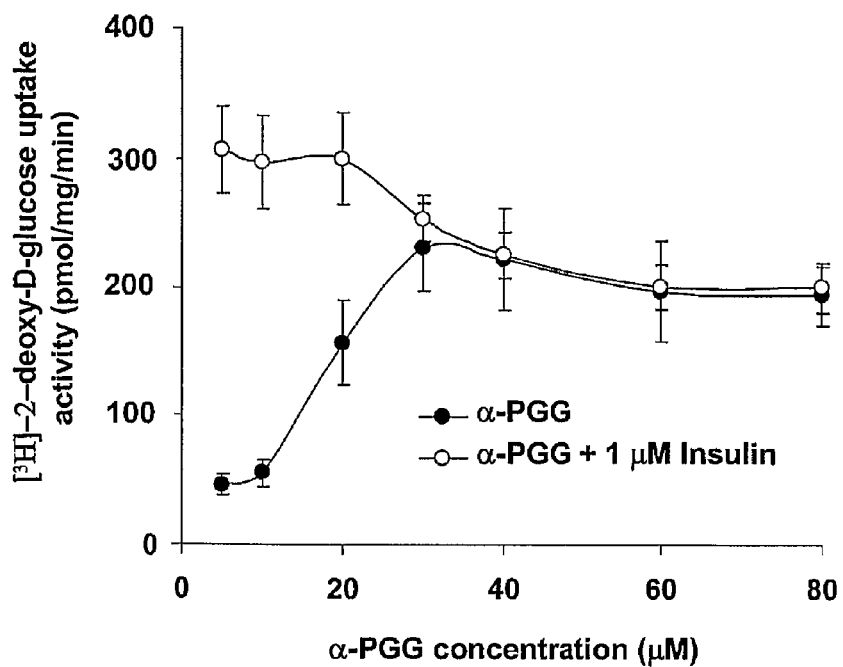

The approximately equimolar mixture of α- and β-PGG (22, FIG. 1A) was synthesized. The compounds were chromatographically separated, and tested individually. α-PGG and β-PGG induced glucose transport in adipocytes in a dose-dependent manner (FIG. 1B). At the 15-30 μM concentration range, α-PGG was consistently 10-20% more active than β-PGG (FIG. 1B, P<0.05 at 15 μM, and P<0.01 at 30 μM). The difference in activity may be accounted for by the structural differences around the anomeric carbon (carbon-1) of the glucose core of the molecules (FIG. 1A). The estimated EC50 for glucose transport activity for α-PGG was 13 μM±2 μM. Since α-PGG showed a higher activity than the β-anomer, it was chosen as our lead compound for the following studies. Addition of α-PGG to insulin reduced the glucose transport activity induced by insulin towards that of α-PGG (FIG. 1C). This result indicates that α-PGG-induced glucose transport activity is not additive or synergistic to that of insulin. α-PPG seems to compete with insulin for the induction of activity.

Figure 2A:
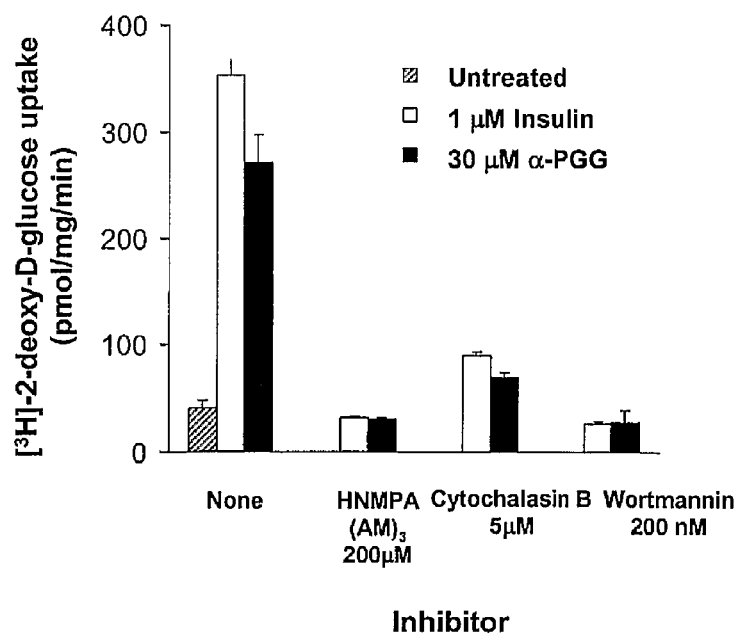
FIG. 2 shows the glucose transport stimulatory activity of PGG is inhibited by antagonists of the insulin signaling pathway and PGG activates the insulin mediated signaling pathway. (A) Glucose transport was measured by determining [$^3$H]-2-deoxyglucose uptake stimulated by either insulin or α-PGG in 3T3-L1 cells in the presence or absence of HNMPA-(AM)$_3$, an inhibitor of IR tyrosine kinase activity (24); wortmannin, an inhibitor of PI 3-kinase (25), or cytochalasin B, an inhibitor of GLUT4 (26), (n=4, mean±SD). (B) Cells were induced by 20 or 40 μM α-PGG or 100 nM insulin for 15 min. Cell lysates were separated by PAGE and analyzed for phosphorylation of IR (in CHO-IR cells) or Akt (in adipocytes) using antibodies specific to the target proteins. (C) Cells were treated with α-PGG and insulin in a fashion similar to (B) and assayed for their respective PI-3 kinase activity with a radioactive TLC method (27). (D) In similar experiments, intact cells were analyzed by confocal microscopy for translocation of GLUT4 using anti-GLUT4 antibodies.
Figure 2B:
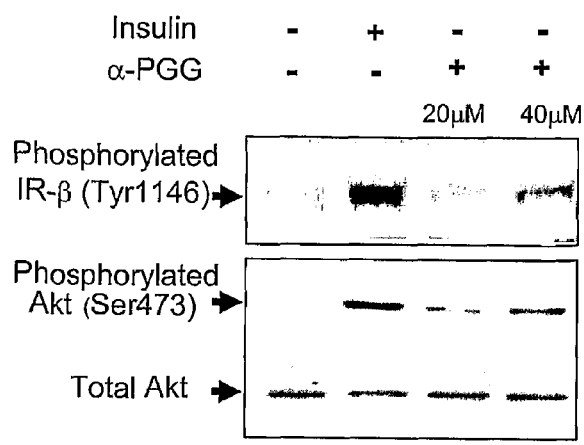
Figure 2C:
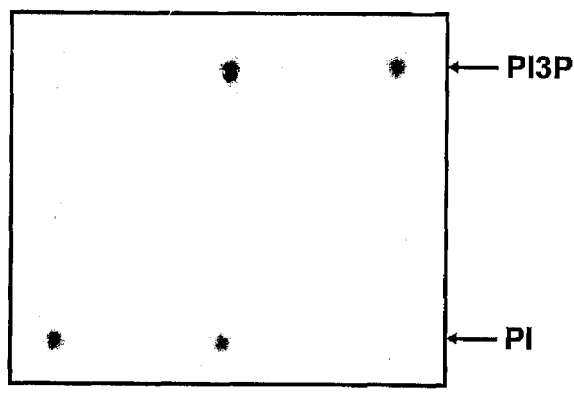
Figure 2D:
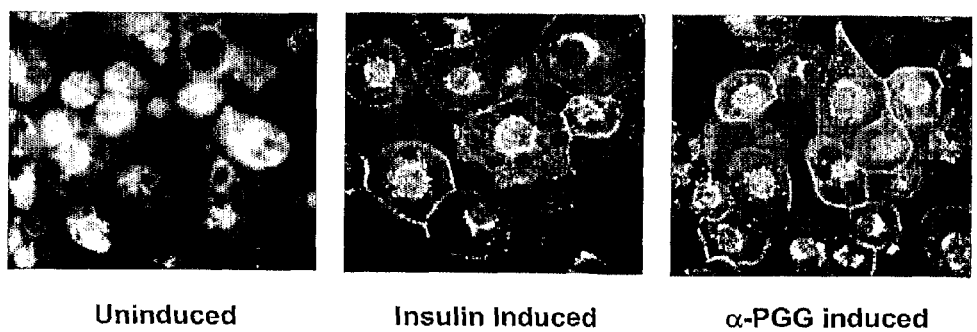

Example 2

α-PGG Activates Protein Factors Involved in the Insulin-Mediated Glucose Transport Signaling Pathway Molecular and cellular studies were initiated to test the hypothesis that PGG activates the insulin-mediated glucose transport signaling pathway. The glucose transport activity induced by α-PGG in adipocytes was completely abolished in the presence of the insulin pathway inhibitors HNMPA-(AM)$_3$, wortmannin, or cytochalasin B (FIG. 2A). Importantly, HNMPA-(AM)$_3$, which inhibits the tyrosine kinase of IR, also completely blocked the activity of α-PGG (FIG. 2A). This result suggests that the target of α-PGG's glucose transport induction is IR, not protein factors downstream from IR. Protein studies revealed that α-PGG induces the phosphorylation of the IR (FIG. 2B) and activates PI-3 kinase (FIG. 2C) in CHO-IR cells, which express significantly more IR than 3T3-L1 adipocytes. It was further shown that Akt was phosphorylated in 3T3-L1 adipocytes in a dose-dependent fashion (FIG. 2B). Immunocyto-chemistry and confocal microscopy established that GLUT4, the effector for insulin-mediated glucose transport in adipocytes is translocated to the plasma membrane after adipocytes are incubated with either α-PGG or insulin (FIG. 2D). These results indicate that α-PGG activates the insulin-mediated glucose transport signaling pathway and strongly suggest that α-PGG acts on the IR.

Example 3

α-PGG Binds to Insulin Receptor and Affects Insulin-IR Binding

Figure 3A:
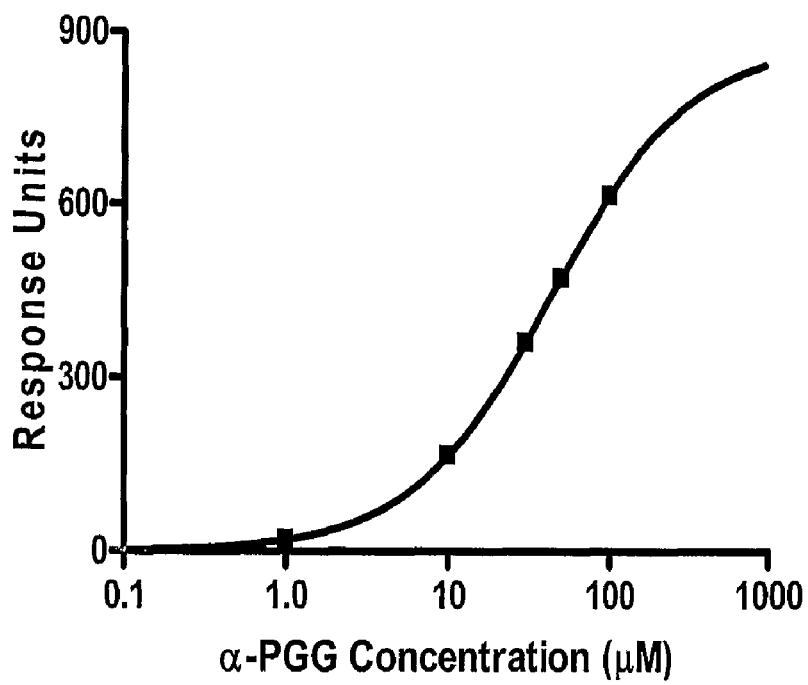
FIG. 3 shows binding of α-PGG to IR and relationship between α-PGG-IR binding and insulin-IR binding. (A) α-PGG binds to IR as measured by a SPR (28). Increasing concentrations of α-PGG was injected into the system to interact with the pure IR attached to the gold surface of the biosensor chip. The binding, represented in arbitrary response units, was automatically plotted against α-PGG concentrations to generate the binding curve. (B) Insulin binding to IR in the absence or presence of α-PGG. Increasing amounts of $^{125}$I-labeled insulin were added to WGA-coated wells containing pre-bound IR isolated from CHO-IR cells in the absence of α-PGG or in the presence of 30 μM or 50 μM of α-PGG. After overnight incubation, removal of excessive ligands, and washing, the bound radioactive insulin was measured. (C) Insulin displacement by α-PGG. Fixed amounts of radioactive insulin (1 nM) were added to each of the WGA-coated wells pre-bound with IR. Increasing amounts of α-PGG were added to the wells to displace the $^{125}$I-labeled insulin. The rest of the assay procedure was the same as in (B). (D) Gel retardation of α-subunit of IR cross-linked with α-PGG. α-PGG was incubated with adipocytes, followed by addition of cross-linker Sulfo-SANPAH (31, 32). The cross-linking reaction was initiated by UV-light. The total protein was subsequently isolated from the treated cells and subjected to Western blot analysis with an anti-IR α-subunit antibody. M designates protein size marker.
Figure 3B:
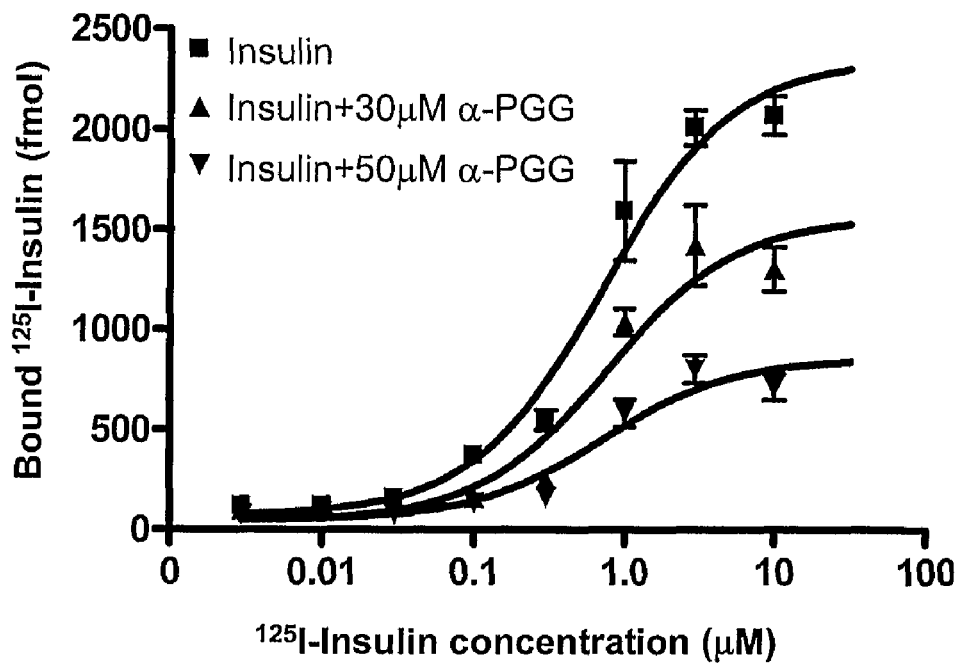

SPR study results indicate that α-PGG binds to pure IR with an apparent binding affinity ($K_d$) of 43±2 μM (FIG. 3A). Together with the findings that α-PGG stimulates insulin-like glucose transport activity (FIG. 1B) and activates protein factors, including IR, involved in the insulin-mediated glucose transport signaling pathway in adipocytes (FIG. 2), this result further supports that the target of α-PGG's glucose transport induction in adipocytes is the IR. The maximal binding ($B_{max}$) for insulin was reduced in a dose-dependent manner with increasing amounts of α-PGG without significantly affecting the $K_d$ (FIG. 3B). This result indicates that α-PGG affected the total binding of insulin without altering insulin's binding affinity to the IR. α-PGG did not bind to insulin, and the inhibitory effect on insulin binding was not a result of α-PGG-insulin binding.

Figure 3C:
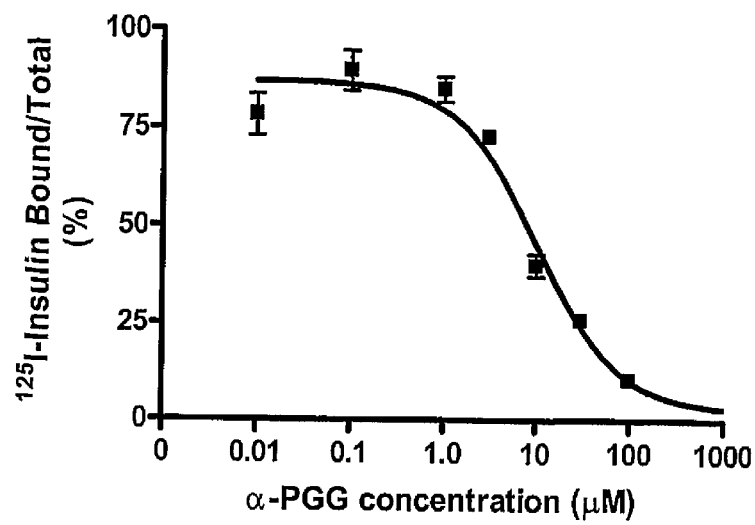

The notion that α-PGG affects insulin-IR binding was further confirmed by the insulin displacement assay in which the IR-bound radioactive insulin was displaced by the increasing amount of α-PGG (FIG. 3C). In this assay, the IC50 for α-PGG was 10±1 μM (FIG. 3C). It was noted that the IC50 was relatively close to the EC50 of α-PGG for the glucose transport stimulatory activity (FIG. 1B: 13 μM±2 μM). The similarities between the EC50, IC50, and $K_d$ (~43 μM±2 μM) suggest that the binding site detected by SPR is the same binding site detected in the WGA binding assay. They further suggest that the binding site shown by the two receptor binding assays may be the site responsible for the glucose transport stimulatory activity of α-PGG.

Figure 3D:
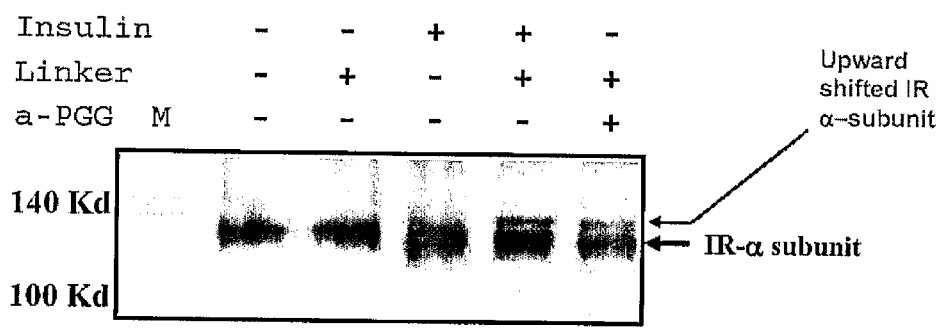

The Western blot analysis using an antibody specific to the α-subunit of IR revealed that, similar to result of the cross linking between insulin and IR, the α-subunit of IR was retarded on a protein gel after the cross-linking reaction between PGG and IR with Sulfo-SANPAH (FIG. 3D). This result strongly suggests that (X-PGG binds to the extracellular α-subunit of the IR. From our binding results (FIG. 3), it was concluded that α-PGG is likely to bind to the α-subunit of the IR but at a site different from the insulin binding site. If α-PGG had bound to the insulin binding site, the $K_d$ of insulin, not $B_{max}$, was likely to be altered. Therefore, PGG is not competitive for the binding of insulin to the insulin binding site. It is a partial agonist to IR for the glucose transport activity (FIG. 1B).

Based upon the results of the pathway studies and the receptor binding studies, it is believed that the following IR binding mechanism for PGG is occurring. α-PGG stimulates glucose transport in adipocytes by directly binding to the IR. α-PGG does not bind to the insulin binding site of the IR, but to another site located on the α-subunit of the IR. The binding of α-PGG to the IR displaces insulin from the insulin binding site. This model is consistent not only with our receptor binding study results (FIG. 3), but also with data that showed that addition of α-PGG to insulin was not additive or synergistic but inhibitory to the glucose transport induction of insulin (FIG. 1C).

Example 4

α-PGG Shows Anti-Diabetic Activity in Diabetic and Obese Mouse Models

Figure 4:
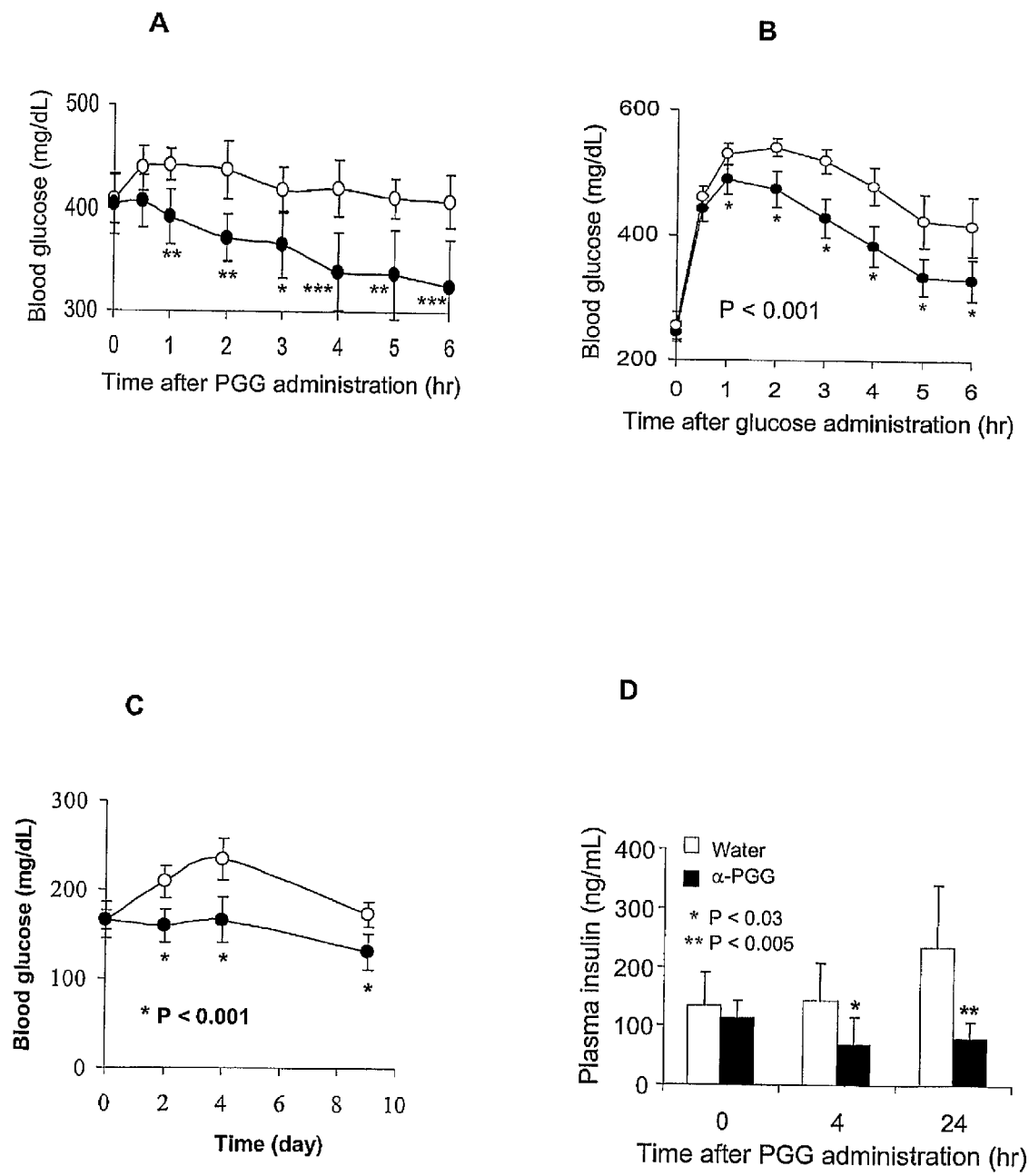
FIG. 4 shows anti-diabetic activities of PGG in diabetic (db/db) or obese (ob/ob) mouse models. Either 6-8 week old male db/db mice or 8-12 week old male ob/ob mice were treated with aqueous solutions of α-PGG by either oral delivery (~10 μL, A & B) or ip injection (~50 μL, C, & D). (n=8-10, mean±SD, one-way ANOVA). α-PGG (●); vehicle (○). α-PGG (20 mg/kg) was orally delivered without glucose to fasting db/db mice (A *, P<0.02; , P<0.01; *, P<0.001) or with glucose (0.4 g/kg body weight) to fasting ob/ob mice (B, glucose tolerance test). α-PGG (20 mg/kg) was ip injected into ob/ob mice on day 0 and day 4 (C). A single ip injection (20 mg/kg) of α-PGG was administered to ob/ob mice (D). Glucose (A, B, C) or insulin (D) was determined from sera or plasma isolated from tail vein blood.

To determine if α-PGG possesses anti-diabetic activity in vivo, it was administered to diabetic and obese mice. A single oral dose of 20 mg/kg α-PGG significantly decreased the blood glucose levels of fasting db/db mice (FIG. 4A). The difference in the blood glucose between the α-PGG treated group and the untreated group became apparent one hour after the treatment, and lasted at least 5 hours (FIG. 4A, P values ranged from 0.02 to 0.001). The glucose level of the α-PGG treated group was about 20% lower than that of the control group 4 to 6 hours after the treatment, although relatively large variations were observed. In ob/ob mice, glucose tolerance was significantly improved by a single oral dose of 20 mg/kg of α-PGG (FIG. 4B). The difference in the blood glucose levels between the α-PGG treated group and the control group became significant one hour after α-PGG administration, and the difference lasted at least 5 h (FIG. 4B, P<0.001). The largest difference in the glucose levels between the two groups was about 20%. For treatments over longer periods of time, ip injection was used to administer the PGG because after several days of polyphenol ingestion, rodents produce salivary proteins that bind and potentially inactivate dietary polyphenols, such as PGG (38). Injections of 20 mg/kg α-PGG on day 0 and day 4 significantly and consistently lowered blood glucose levels in ob/ob mice compared to the vehicle-treated controls (FIG. 4C, P<0.001). Furthermore, significantly lower plasma insulin levels were found in the α-PGG-treated hyperinsulinemic ob/ob mice compared to the controls (FIG. 4D, P values ranged from 0.03 to 0.005). The anti-hyperinsulinemic effects of α-PGG lasted at least 24 hours (FIG. 4D). No significant changes in body weight, food intake, or physical activity were observed in α-PGG-treated mice compared to the control mice. It has been shown that α-PGG effectively reduces blood glucose and insulin levels in diabetic and obese animal models (FIG. 5).

Several anti-diabetic small molecule insulin mimetics have been reported. Most of these compounds bind and activate the IR and have hyperglycemic effects in animals. The use of insulin mimetics to reduce the blood glucose level is a well-established anti-diabetes strategy. α-PGG distinguishes itself from other drugs by the fact that it not only stimulates glucose transport, but it also inhibits the differentiation of preadipocytes into adipocytes. This suggests that, unlike most other anti-diabetic drugs, α-PGG may reduce blood glucose without increasing adiposity.

What is claimed is:

1. A method of identifying a candidate molecule that activates glucose transport, comprising:

a.) combining an insulin receptor molecule and insulin under conditions suitable for specific interaction between said insulin receptor molecule and insulin resulting in an equilibrium binding state;

b.) further combining said candidate molecule with said combined insulin receptor molecule and insulin under conditions suitable for specific interaction between said candidate molecule and combined insulin receptor molecule and insulin; and c.) determining the ability of said candidate molecule to bind to said combined insulin receptor molecule and insulin;

d.) determining whether said candidate molecule activates glucose transport;

e.) determining whether said candidate molecule influences maximal binding ($B_{max}$) of insulin to said insulin receptor in a dose dependent manner without materially altering insulin's binding affinity ($K_d$) for said insulin receptor; and f.) selecting a candidate molecule that binds to said combined insulin receptor molecule and insulin, activates glucose transport, and decreases maximal binding ($B_{max}$) of insulin to said insulin receptor in a dose dependent manner without materially altering insulin's binding affinity ($K_d$) for said insulin receptor.

2. The method of claim 1, wherein the step of determining the ability of said candidate molecule to bind to said combined insulin receptor molecule and insulin results in a displacement of insulin from said insulin receptor molecule in a non-competitive manner.

3. The method of claim 2, wherein said candidate molecule displays 50% of its ability to displace insulin from said insulin receptor molecule ($IC_{50}$) at a concentration equal to or less than approximately 10 μM.

4. The method of claim 1, wherein said insulin receptor molecule comprises at least one alpha subunit and at least one beta subunit.

5. The method of claim 4, wherein the step of determining the ability of said candidate molecule to bind to said combined insulin receptor molecule and insulin involves determining the ability of said candidate molecule to bind to said at least one alpha subunit of said insulin receptor molecule.

* * * * *

SEQUENCE LISTING

<160> NUMBER OF SEQ ID NOS: 2

<210> SEQ ID NO 1
<211> LENGTH: 1382
<212> TYPE: PRT
<213> ORGANISM: Homo sapiens

<400> SEQUENCE: 1

```
Met Gly Thr Gly Gly Arg Arg Gly Ala Ala Ala Ala Pro Leu Leu Val
1               5                   10                  15

Ala Val Ala Ala Leu Leu Leu Gly Ala Ala Gly His Leu Tyr Pro Gly
            20                  25                  30

Glu Val Cys Pro Gly Met Asp Ile Arg Asn Asn Leu Thr Arg Leu His
        35                  40                  45

Glu Leu Glu Asn Cys Ser Val Ile Glu Gly His Leu Gln Ile Leu Leu
    50                  55                  60

Met Phe Lys Thr Arg Pro Glu Asp Phe Arg Asp Leu Ser Phe Pro Lys
65                  70                  75                  80

Leu Ile Met Ile Thr Asp Tyr Leu Leu Leu Phe Arg Val Tyr Gly Leu
                85                  90                  95

Glu Ser Leu Lys Asp Leu Phe Pro Asn Leu Thr Val Ile Arg Gly Ser
            100                 105                 110

Arg Leu Phe Phe Asn Tyr Ala Leu Val Ile Phe Glu Met Val His Leu
        115                 120                 125

Lys Glu Leu Gly Leu Tyr Asn Leu Met Asn Ile Thr Arg Gly Ser Val
    130                 135                 140

Arg Ile Glu Lys Asn Asn Glu Leu Cys Tyr Leu Ala Thr Ile Asp Trp
145                 150                 155                 160

Ser Arg Ile Leu Asp Ser Val Glu Asp Asn His Ile Val Leu Asn Lys
                165                 170                 175
```

```
Asp Asp Asn Glu Glu Cys Gly Asp Ile Cys Pro Gly Thr Ala Lys Gly
            180                 185                 190

Lys Thr Asn Cys Pro Ala Thr Val Ile Asn Gly Gln Phe Val Glu Arg
            195                 200                 205

Cys Trp Thr His Ser His Cys Gln Lys Val Cys Pro Thr Ile Cys Lys
            210                 215                 220

Ser His Gly Cys Thr Ala Glu Gly Leu Cys Cys His Ser Glu Cys Leu
225                 230                 235                 240

Gly Asn Cys Ser Gln Pro Asp Asp Pro Thr Lys Cys Val Ala Cys Arg
                245                 250                 255

Asn Phe Tyr Leu Asp Gly Arg Cys Val Glu Thr Cys Pro Pro Pro Tyr
            260                 265                 270

Tyr His Phe Gln Asp Trp Arg Cys Val Asn Phe Ser Phe Cys Gln Asp
            275                 280                 285

Leu His His Lys Cys Lys Asn Ser Arg Arg Gln Gly Cys His Gln Tyr
            290                 295                 300

Val Ile His Asn Asn Lys Cys Ile Pro Glu Cys Pro Ser Gly Tyr Thr
305                 310                 315                 320

Met Asn Ser Ser Asn Leu Leu Cys Thr Pro Cys Leu Gly Pro Cys Pro
                325                 330                 335

Lys Val Cys His Leu Leu Glu Gly Glu Lys Thr Ile Asp Ser Val Thr
            340                 345                 350

Ser Ala Gln Glu Leu Arg Gly Cys Thr Val Ile Asn Gly Ser Leu Ile
            355                 360                 365

Ile Asn Ile Arg Gly Gly Asn Asn Leu Ala Ala Glu Leu Glu Ala Asn
            370                 375                 380

Leu Gly Leu Ile Glu Glu Ile Ser Gly Tyr Leu Lys Ile Arg Arg Ser
385                 390                 395                 400

Tyr Ala Leu Val Ser Leu Ser Phe Phe Arg Lys Leu Arg Leu Ile Arg
                405                 410                 415

Gly Glu Thr Leu Glu Ile Gly Asn Tyr Ser Phe Tyr Ala Leu Asp Asn
            420                 425                 430

Gln Asn Leu Arg Gln Leu Trp Asp Trp Ser Lys His Asn Leu Thr Thr
            435                 440                 445

Thr Gln Gly Lys Leu Phe Phe His Tyr Asn Pro Lys Leu Cys Leu Ser
            450                 455                 460

Glu Ile His Lys Met Glu Glu Val Ser Gly Thr Lys Gly Arg Gln Glu
465                 470                 475                 480

Arg Asn Asp Ile Ala Leu Lys Thr Asn Gly Asp Lys Ala Ser Cys Glu
                485                 490                 495

Asn Glu Leu Leu Lys Phe Ser Tyr Ile Arg Thr Ser Phe Asp Lys Ile
            500                 505                 510

Leu Leu Arg Trp Glu Pro Tyr Trp Pro Pro Asp Phe Arg Asp Leu Leu
            515                 520                 525

Gly Phe Met Leu Phe Tyr Lys Glu Ala Pro Tyr Gln Asn Val Thr Glu
530                 535                 540

Phe Asp Gly Gln Asp Ala Cys Gly Ser Asn Ser Trp Thr Val Val Asp
545                 550                 555                 560

Ile Asp Pro Pro Leu Arg Ser Asn Asp Pro Lys Ser Gln Asn His Pro
                565                 570                 575

Gly Trp Leu Met Arg Gly Leu Lys Pro Trp Thr Gln Tyr Ala Ile Phe
            580                 585                 590
```

```
            Val Lys Thr Leu Val Thr Phe Ser Asp Glu Arg Arg Thr Tyr Gly Ala
                    595                 600                 605

Lys Ser Asp Ile Ile Tyr Val Gln Thr Asp Ala Thr Asn Pro Ser Val
                610                 615                 620

Pro Leu Asp Pro Ile Ser Val Ser Asn Ser Ser Gln Ile Ile Leu
            625                 630                 635                 640

Lys Trp Lys Pro Pro Ser Asp Pro Asn Gly Asn Ile Thr His Tyr Leu
                            645                 650                 655

Val Phe Trp Glu Arg Gln Ala Glu Asp Ser Glu Leu Phe Glu Leu Asp
                        660                 665                 670

Tyr Cys Leu Lys Gly Leu Lys Leu Pro Ser Arg Thr Trp Ser Pro Pro
                        675                 680                 685

Phe Glu Ser Glu Asp Ser Gln Lys His Asn Gln Ser Glu Tyr Glu Asp
            690                 695                 700

Ser Ala Gly Glu Cys Cys Ser Cys Pro Lys Thr Asp Ser Gln Ile Leu
            705                 710                 715                 720

Lys Glu Leu Glu Glu Ser Ser Phe Arg Lys Thr Phe Glu Asp Tyr Leu
                            725                 730                 735

His Asn Val Val Phe Val Pro Arg Lys Thr Ser Ser Gly Thr Gly Ala
                        740                 745                 750

Glu Asp Pro Arg Pro Ser Arg Lys Arg Arg Ser Leu Gly Asp Val Gly
                        755                 760                 765

Asn Val Thr Val Ala Val Pro Thr Val Ala Ala Phe Pro Asn Thr Ser
                    770                 775                 780

Ser Thr Ser Val Pro Thr Ser Pro Glu Glu His Arg Pro Phe Glu Lys
            785                 790                 795                 800

Val Val Asn Lys Glu Ser Leu Val Ile Ser Gly Leu Arg His Phe Thr
                            805                 810                 815

Gly Tyr Arg Ile Glu Leu Gln Ala Cys Asn Gln Asp Thr Pro Glu Glu
                        820                 825                 830

Arg Cys Ser Val Ala Ala Tyr Val Ser Ala Arg Thr Met Pro Glu Ala
                        835                 840                 845

Lys Ala Asp Asp Ile Val Gly Pro Val Thr His Glu Ile Phe Glu Asn
                850                 855                 860

Asn Val Val His Leu Met Trp Gln Glu Pro Lys Glu Pro Asn Gly Leu
            865                 870                 875                 880

Ile Val Leu Tyr Glu Val Ser Tyr Arg Arg Tyr Gly Asp Glu Glu Leu
                            885                 890                 895

His Leu Cys Val Ser Arg Lys His Phe Ala Leu Glu Arg Gly Cys Arg
                        900                 905                 910

Leu Arg Gly Leu Ser Pro Gly Asn Tyr Ser Val Arg Ile Arg Ala Thr
                        915                 920                 925

Ser Leu Ala Gly Asn Gly Ser Trp Thr Glu Pro Thr Tyr Phe Tyr Val
                    930                 935                 940

Thr Asp Tyr Leu Asp Val Pro Ser Asn Ile Ala Lys Ile Ile Ile Gly
            945                 950                 955                 960

Pro Leu Ile Phe Val Phe Leu Phe Ser Val Val Ile Gly Ser Ile Tyr
                            965                 970                 975

Leu Phe Leu Arg Lys Arg Gln Pro Asp Gly Pro Leu Gly Pro Leu Tyr
                        980                 985                 990

Ala Ser Ser Asn Pro Glu Tyr Leu  Ser Ala Ser Asp Val  Phe Pro Cys
                        995                 1000                1005

Ser Val  Tyr Val Pro Asp Glu  Trp Glu Val Ser Arg  Glu Lys Ile
```

-continued

```
                1010                1015                1020

Thr Leu Leu Arg Glu Leu Gly Gln Gly Ser Phe Gly Met Val Tyr
    1025                1030                1035

Glu Gly Asn Ala Arg Asp Ile Ile Lys Gly Ala Glu Thr Arg
    1040                1045                1050

Val Ala Val Lys Thr Val Asn Glu Ser Ala Ser Leu Arg Glu Arg
    1055                1060                1065

Ile Glu Phe Leu Asn Glu Ala Ser Val Met Lys Gly Phe Thr Cys
    1070                1075                1080

His His Val Val Arg Leu Leu Gly Val Val Ser Lys Gly Gln Pro
    1085                1090                1095

Thr Leu Val Val Met Glu Leu Met Ala His Gly Asp Leu Lys Ser
    1100                1105                1110

Tyr Leu Arg Ser Leu Arg Pro Glu Ala Glu Asn Asn Pro Gly Arg
    1115                1120                1125

Pro Pro Pro Thr Leu Gln Glu Met Ile Gln Met Ala Ala Glu Ile
    1130                1135                1140

Ala Asp Gly Met Ala Tyr Leu Asn Ala Lys Lys Phe Val His Arg
    1145                1150                1155

Asp Leu Ala Ala Arg Asn Cys Met Val Ala His Asp Phe Thr Val
    1160                1165                1170

Lys Ile Gly Asp Phe Gly Met Thr Arg Asp Ile Tyr Glu Thr Asp
    1175                1180                1185

Tyr Tyr Arg Lys Gly Gly Lys Gly Leu Leu Pro Val Arg Trp Met
    1190                1195                1200

Ala Pro Glu Ser Leu Lys Asp Gly Val Phe Thr Thr Ser Ser Asp
    1205                1210                1215

Met Trp Ser Phe Gly Val Val Leu Trp Glu Ile Thr Ser Leu Ala
    1220                1225                1230

Glu Gln Pro Tyr Gln Gly Leu Ser Asn Glu Gln Val Leu Lys Phe
    1235                1240                1245

Val Met Asp Gly Gly Tyr Leu Asp Gln Pro Asp Asn Cys Pro Glu
    1250                1255                1260

Arg Val Thr Asp Leu Met Arg Met Cys Trp Gln Phe Asn Pro Lys
    1265                1270                1275

Met Arg Pro Thr Phe Leu Glu Ile Val Asn Leu Leu Lys Asp Asp
    1280                1285                1290

Leu His Pro Ser Phe Pro Glu Val Ser Phe Phe His Ser Glu Glu
    1295                1300                1305

Asn Lys Ala Pro Glu Ser Glu Glu Leu Glu Met Glu Phe Glu Asp
    1310                1315                1320

Met Glu Asn Val Pro Leu Asp Arg Ser Ser His Cys Gln Arg Glu
    1325                1330                1335

Glu Ala Gly Gly Arg Asp Gly Gly Ser Ser Leu Gly Phe Lys Arg
    1340                1345                1350

Ser Tyr Glu Glu His Ile Pro Tyr Thr His Met Asn Gly Gly Lys
    1355                1360                1365

Lys Asn Gly Arg Ile Leu Thr Leu Pro Arg Ser Asn Pro Ser
    1370                1375                1380

<210> SEQ ID NO 2
<211> LENGTH: 734
<212> TYPE: PRT
<213> ORGANISM: Homo sapiens
```

```
<400> SEQUENCE: 2

His Leu Tyr Pro Gly Glu Val Cys Pro Gly Met Asp Ile Arg Asn Asn
  1               5                  10                  15

Leu Thr Arg Leu His Glu Leu Glu Asn Cys Ser Val Ile Glu Gly His
             20                  25                  30

Leu Gln Ile Leu Leu Met Phe Lys Thr Arg Pro Glu Asp Phe Arg Asp
         35                  40                  45

Leu Ser Phe Pro Lys Leu Ile Met Ile Thr Asp Tyr Leu Leu Leu Phe
     50                  55                  60

Arg Val Tyr Gly Leu Glu Ser Leu Lys Asp Leu Phe Pro Asn Leu Thr
 65                  70                  75                  80

Val Ile Arg Gly Ser Arg Leu Phe Phe Asn Tyr Ala Leu Val Ile Phe
                 85                  90                  95

Glu Met Val His Leu Lys Glu Leu Gly Leu Tyr Asn Leu Met Asn Ile
                100                 105                 110

Thr Arg Gly Ser Val Arg Ile Glu Lys Asn Asn Glu Leu Cys Tyr Leu
            115                 120                 125

Ala Thr Ile Asp Trp Ser Arg Ile Leu Asp Ser Val Glu Asp Asn His
        130                 135                 140

Ile Val Leu Asn Lys Asp Asp Asn Glu Glu Cys Gly Asp Ile Cys Pro
145                 150                 155                 160

Gly Thr Ala Lys Gly Lys Thr Asn Cys Pro Ala Thr Val Ile Asn Gly
                165                 170                 175

Gln Phe Val Glu Arg Cys Trp Thr His Ser His Cys Gln Lys Val Cys
            180                 185                 190

Pro Thr Ile Cys Lys Ser His Gly Cys Thr Ala Glu Gly Leu Cys Cys
            195                 200                 205

His Ser Glu Cys Leu Gly Asn Cys Ser Gln Pro Asp Asp Pro Thr Lys
        210                 215                 220

Cys Val Ala Cys Arg Asn Phe Tyr Leu Asp Gly Arg Cys Val Glu Thr
225                 230                 235                 240

Cys Pro Pro Pro Tyr Tyr His Phe Gln Asp Trp Arg Cys Val Asn Phe
                245                 250                 255

Ser Phe Cys Gln Asp Leu His His Lys Cys Lys Asn Ser Arg Arg Gln
            260                 265                 270

Gly Cys His Gln Tyr Val Ile His Asn Asn Lys Cys Ile Pro Glu Cys
        275                 280                 285

Pro Ser Gly Tyr Thr Met Asn Ser Ser Asn Leu Leu Cys Thr Pro Cys
    290                 295                 300

Leu Gly Pro Cys Pro Lys Val Cys His Leu Leu Glu Gly Glu Lys Thr
305                 310                 315                 320

Ile Asp Ser Val Thr Ser Ala Gln Glu Leu Arg Gly Cys Thr Val Ile
                325                 330                 335

Asn Gly Ser Leu Ile Ile Asn Ile Arg Gly Gly Asn Asn Leu Ala Ala
            340                 345                 350

Glu Leu Glu Ala Asn Leu Gly Leu Ile Glu Glu Ile Ser Gly Tyr Leu
        355                 360                 365

Lys Ile Arg Arg Ser Tyr Ala Leu Val Ser Leu Ser Phe Phe Arg Lys
    370                 375                 380

Leu Arg Leu Ile Arg Gly Glu Thr Leu Glu Ile Gly Asn Tyr Ser Phe
385                 390                 395                 400

Tyr Ala Leu Asp Asn Gln Asn Leu Arg Gln Leu Trp Asp Trp Ser Lys
```

-continued

```
                         405                 410                 415
His Asn Leu Thr Thr Thr Gln Gly Lys Leu Phe Phe His Tyr Asn Pro
                420                 425                 430
Lys Leu Cys Leu Ser Glu Ile His Lys Met Glu Glu Val Ser Gly Thr
                435                 440                 445
Lys Gly Arg Gln Glu Arg Asn Asp Ile Ala Leu Lys Thr Asn Gly Asp
                450                 455                 460
Lys Ala Ser Cys Glu Asn Glu Leu Leu Lys Phe Ser Tyr Ile Arg Thr
465                 470                 475                 480
Ser Phe Asp Lys Ile Leu Leu Arg Trp Glu Pro Tyr Trp Pro Pro Asp
                485                 490                 495
Phe Arg Asp Leu Leu Gly Phe Met Leu Phe Tyr Lys Glu Ala Pro Tyr
                500                 505                 510
Gln Asn Val Thr Glu Phe Asp Gly Gln Asp Ala Cys Gly Ser Asn Ser
                515                 520                 525
Trp Thr Val Val Asp Ile Asp Pro Pro Leu Arg Ser Asn Asp Pro Lys
                530                 535                 540
Ser Gln Asn His Pro Gly Trp Leu Met Arg Gly Leu Lys Pro Trp Thr
545                 550                 555                 560
Gln Tyr Ala Ile Phe Val Lys Thr Leu Val Thr Phe Ser Asp Glu Arg
                565                 570                 575
Thr Tyr Gly Ala Lys Ser Asp Ile Ile Tyr Val Gln Thr Asp Ala Thr
                580                 585                 590
Asn Pro Ser Val Pro Leu Asp Pro Ile Ser Val Ser Asn Ser Ser Ser
                595                 600                 605
Gln Ile Ile Leu Lys Trp Lys Pro Pro Ser Asp Pro Asn Gly Asn Ile
                610                 615                 620
Thr His Tyr Leu Val Phe Trp Glu Arg Gln Ala Glu Asp Ser Glu Leu
625                 630                 635                 640
Phe Glu Leu Asp Tyr Cys Leu Lys Gly Leu Lys Leu Pro Ser Arg Thr
                645                 650                 655
Trp Ser Pro Pro Phe Glu Ser Glu Asp Ser Gln Lys His Asn Gln Ser
                660                 665                 670
Glu Tyr Glu Asp Ser Ala Gly Glu Cys Cys Ser Cys Pro Lys Thr Asp
                675                 680                 685
Ser Gln Ile Leu Lys Glu Leu Glu Glu Ser Ser Phe Arg Lys Thr Phe
                690                 695                 700
Glu Asp Tyr Leu His Asn Val Val Phe Val Pro Arg Lys Thr Ser Ser
705                 710                 715                 720
Gly Thr Gly Ala Glu Asp Pro Arg Pro Ser Arg Lys Arg Arg
                725                 730
```